US012446841B2

(12) United States Patent
Thibault et al.

(10) Patent No.: US 12,446,841 B2
(45) Date of Patent: Oct. 21, 2025

(54) SYSTEMS AND METHODS FOR COMPUTED TOMOGRAPHY

(71) Applicant: GE Precision Healthcare LLC, Wauwatosa, WI (US)

(72) Inventors: Jean-Baptiste Thibault, Waukesha, WI (US); John Howard Londt, Waukesha, WI (US); John Boudry, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 222 days.

(21) Appl. No.: 18/051,433

(22) Filed: Oct. 31, 2022

(65) Prior Publication Data

US 2024/0138786 A1 May 2, 2024

(51) Int. Cl.

| | |
|---|---|
| ***A61B 6/40*** | (2024.01) |
| ***A61B 6/00*** | (2006.01) |
| ***A61B 6/03*** | (2006.01) |
| ***A61B 6/58*** | (2024.01) |

(52) U.S. Cl.

CPC ............ *A61B 6/4021* (2013.01); *A61B 6/032* (2013.01); *A61B 6/5205* (2013.01); *A61B 6/54* (2013.01); *A61B 6/582* (2013.01)

(58) Field of Classification Search

CPC ..... A61B 6/4021; A61B 6/032; A61B 6/5205; A61B 6/54; A61B 6/582; A61B 6/488; A61B 6/542; A61B 6/4085; H05G 1/52

See application file for complete search history.

(56) References Cited

U.S. PATENT DOCUMENTS

| | | | | |
|---|---|---|---|---|
| 7,249,886 | B1 | 7/2007 | Chao et al. | |
| 7,409,043 | B1 | 8/2008 | Dunham et al. | |
| 8,457,282 | B2 * | 6/2013 | Baorui | A61B 6/032 378/22 |

(Continued)

FOREIGN PATENT DOCUMENTS

| | | |
|---|---|---|
| JP | H04231941 A | 8/1992 |
| JP | 2007054528 A | 3/2007 |

(Continued)

OTHER PUBLICATIONS

EP application 23203458.7 filed Oct. 13, 2023—Search Report issued Mar. 6, 2024; 8 pages.

(Continued)

*Primary Examiner* — David P Porta
*Assistant Examiner* — Mamadou Faye
(74) *Attorney, Agent, or Firm* — McCoy Russell LLP

(57) ABSTRACT

Methods and systems are provided for increasing a quality of computed tomography (CT) images. In one embodiment, a CT system comprises an X-ray tube and an X-ray controller including one or more processors having executable instructions stored in a non-transitory memory of the CT system that, when executed, cause the one or more processors to, during a first view of a CT scan of an object, focus an electron beam at a first focal spot on a target of the X-ray tube, the first focal spot of a first size; during a second view of the CT scan, focus the electron beam at a second focal spot on the target, the second focal spot of a second size different from the first size; and reconstruct an image of the object from projection data including the first view and the second view.

20 Claims, 7 Drawing Sheets

(56) References Cited

U.S. PATENT DOCUMENTS

| | | | | |
|---|---|---|---|---|
| 10,535,491 | B2 | 1/2020 | Rommel et al. | |
| 11,039,809 | B2 | 6/2021 | Lemaitre et al. | |
| 2004/0264628 | A1 * | 12/2004 | Besson | G21K 1/10 378/5 |
| 2012/0082292 | A1 | 4/2012 | Zou | |
| 2016/0235382 | A1 * | 8/2016 | Besson | A61B 6/032 |
| 2018/0082818 | A1 * | 3/2018 | Meiler | H01J 35/025 |
| 2018/0235564 | A1 * | 8/2018 | Jain | A61B 6/50 |
| 2019/0247005 | A1 * | 8/2019 | Ikhlef | A61B 6/03 |
| 2021/0007210 | A1 * | 1/2021 | Steadman Booker | H01J 35/153 |
| 2022/0110599 | A1 * | 4/2022 | Pelc | G06T 11/006 |

FOREIGN PATENT DOCUMENTS

| | | | |
|---|---|---|---|
| JP | 2011024806 | A | 2/2011 |
| JP | 2015092953 | A | 5/2015 |
| JP | 2016034374 | A | 3/2016 |
| JP | 2018049813 | A | 3/2018 |
| JP | 2020141808 | A | 9/2020 |
| JP | 2022046946 | A | 3/2022 |

OTHER PUBLICATIONS

JP H04231941 Translation of Abstract, EPO Patent Abstracts of Japan, 1992; 1 page.

JP application 2023-171719 filed Oct. 3, 2023—Office Action issued Nov. 6, 2024; Machine Translation; 8 pages.

JP application 2023-171719 filed Oct. 3, 2023—Office Action issued Jan. 29, 2025; Machine Translation; 9 pages.

JP2022046946 English Abstract; obtained Espacenet.com Feb. 6, 2025; 1 page.

JP2007054528 English Abstract; obtained Espacenet.com Feb. 6, 2025; 1 page.

JP2015092953 English Abstract; obtained Espacenet.com Feb. 6, 2025; 1 page.

JP2011024806 English Abstract; obtained Espacenet.com Feb. 6, 2025; 1 page.

JP2020141808 English Abstract; obtained Espacenet.com Feb. 6, 2025; 1 page.

JP2016034374 English Abstract; obtained Espacenet.com Feb. 6, 2025; 1 page.

JP2018049813 English Abstract; obtained Espacenet.com Feb. 6, 2025; 1 page.

* cited by examiner

SYSTEMS AND METHODS FOR COMPUTED TOMOGRAPHY

TECHNICAL FIELD

Embodiments of the subject matter disclosed herein relate to medical imaging, and more particularly, to computerized tomography imaging systems.

BACKGROUND

In computed tomography (CT) imaging systems, an electron beam generated by a cathode is directed towards a target within an X-ray tube. In some embodiments, the target may be an anode, while in other embodiments, the X-ray tube may include an anode separate from the target. A fan-shaped or cone-shaped beam of X-rays produced by electrons colliding with the target is directed towards an object, such as a patient. After being attenuated by the object, the X-rays impinge upon an array of radiation detectors, generating an image. An area of focus in the image may depend on a focal spot of the electron beam on the target, where the focal spot is created by focusing the electron beam using focusing electrodes and/or magnets. An image generated using a larger focal spot may have a lower spatial resolution, and an image generated using a smaller focal spot may have a higher spatial resolution. Thus, to generate images with a desired area of focus and a desired spatial resolution, a CT system may be configured to generate a focal spot of a desired size and/or shape to use across all views of a scan.

In CT scans, it is common to modulate X-ray flux as a function of view angle through the scanned object (also known as mA modulation) in order to optimize radiation dose and image quality performance throughout the scanned volume. When selecting CT exposure parameters for mA modulated scans, a CT system usually chooses the smallest available focal spot that supports the maximum instantaneous tube power required to produce the highest prescribed current, without damage to the tube. That focal spot size may not be changed throughout the exposure.

However, the inventors herein have recognized potential issues with focal spot sizing in CT systems. In particular, a spatial resolution of images reconstructed using the smallest available focal spot may be high for views at the highest prescribed current, but lower for views at lower prescribed currents. For example, a small portion of the total number of views may be scanned at a high current, and a larger portion of the total number of views may be scanned at lower currents. If the focal spot size is selected for the highest prescribed current, that focal spot size may be too large to produce high quality images for views at the lower currents. As a result, reconstructed images where the larger portion of the total number of views is scanned at lower currents may include artifacts such as blurred edges between scanned objects.

A focal spot position may be modulated during an exposure (a.k.a "focal spot wobble" or "flying focal spot"). The intention of dynamically changing focal spot position from view to view is to increase sampling rate to reduce aliasing and allow using higher frequency kernels in reconstruction to achieve higher spatial resolution. However, overall spatial resolution remains constrained by overall focal spot size. While x-ray tubes are generally capable of changing focal spot controls as a function of current, either electrostatically or magnetically, tubes may be commanded to use the same focal spot size throughout a continuous X-ray exposure.

Other approaches have been taken to adjust focal spot size during a single exposure (e.g., between views). However, the approaches rely on switching X-rays off to switch from a first focal spot size to a second focal spot size, rather than during the continuous X-ray exposure. For example, changing focal spot size as a function of current is used in interventional X-ray, where pulsed X-ray exposures are used. Each pulse may be done at a different current setting, and therefore with a different focal spot size. However, the focal spot size remains fixed during a sub-exposure (e.g., from x-ray on to x-ray off), and the focal spot size is not modulated during a continuous X-ray exposure between x-ray on to x-ray off.

SUMMARY

The current disclosure at least partially addresses one or more of the above identified issues by a computed tomography (CT) system, comprising an X-ray tube and an X-ray controller including one or more processors having executable instructions stored in a non-transitory memory of the CT system that, when executed, cause the one or more processors to, during a first view of a CT scan of an object, focus an electron beam at a first focal spot on a target of the X-ray tube, the first focal spot of a first size; during a second view of the CT scan, focus the electron beam at a second focal spot on the target, the second focal spot of a second size different from the first size; and reconstruct an image of the object from projection data including the first view and the second view. The size of the first focal spot and the second focal spot may be selected based on a current applied during a respective view. If the current is high, a larger focal spot may be selected, and if the current is low, a smaller focal spot may be selected. For example, if the current is modulated across views in accordance with an mA modulation profile, the first focal spot may be selected for a first group of views, where the current is within a first current range. When the current leaves the first current range and enters a second current range (e.g., more current or less current is applied), the second focal spot may be selected for a second group of views, where the current is in the second current range, and so on for additional current ranges. By adjusting the size of the focal spot during the exposure, an overall spatial resolution of reconstructed images may be increased, producing higher quality images without generating artifacts.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
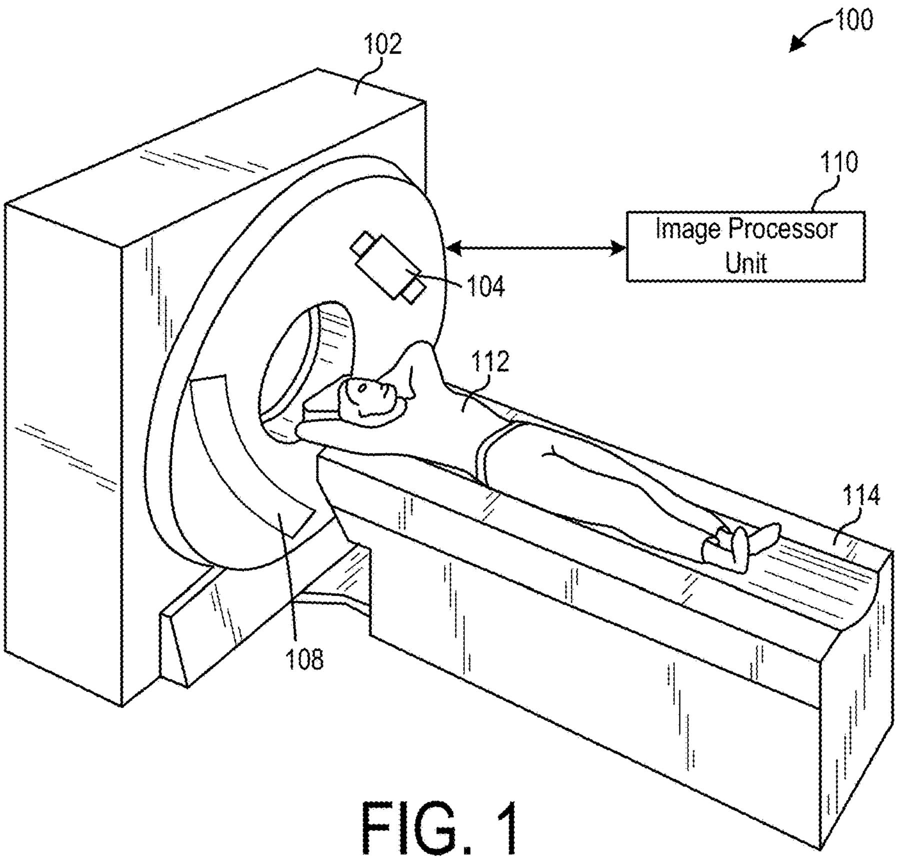
FIG. 1 shows a pictorial view of an imaging system, in accordance with one or more embodiments of the present disclosure.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

This description and embodiments of the subject matter disclosed herein relate to methods and systems for a computed tomography imaging (CT) system. Typically, in CT systems, an X-ray source emits a fan-shaped beam or a cone-shaped beam towards an object, such as a patient. Generally, in CT systems the X-ray source and the detector array are rotated about a gantry within an imaging plane and around the patient, and images are generated from projection data at a plurality of views at different view angles. For example, for one rotation of the X-ray source, 984 views may be generated by the CT system.

Images reconstructed from the projection data may be 3D cross-sectional images of the scanned object generated from a plurality of projection views collected at a plurality of projection angles around the object. Each projection view measures attenuation path lengths through the scanned object over the face of the detector when illuminated by the x-rays emanating from the focal spot in the x-ray source. A plurality of projection views are acquired at different projection view angles as the x-ray source rotates within the gantry around the scanned object. As the x-ray source rotates through each rotational position, the view angle changes, resulting in a measure of different attenuation path lengths through the scanned object being illuminated. Complete projection data is acquired over a minimum of 180 degrees plus fan angle, also known as short scan angular range. Projection data can also be acquired over a full rotation around the scanned object for the reconstruction of a single axial cross-sectional image, or over more than a full rotation to cover a certain extent of the scanned object along the long axis of the scanner, from which multiple cross-sectional images of the scanned object can be reconstructed. A single cross-sectional 2D image reconstruction requires the back-projection of a plurality of projection views over a minimum of a short scan angular range (for a half scan reconstruction), or a full angular rotation around the object (for a full scan reconstruction). After multiple cross-sectional 2D images of the scanned object are reconstructed, a 3D volumetric image may be generated from the multiple cross sections of the scanned object, which may be viewed on a display device. Using less than the minimum number of projection views typically results in an incomplete or partial image reconstruction that may not represent the scanned object well. It should be appreciated that, as used herein, the word "image" used alone typically refers to a 2D cross-sectional image.

The beam, after being attenuated by the patient, impinges upon an array of radiation detectors. The X-ray detector or detector array typically includes a collimator for collimating X-ray beams received at the detector, a scintillator disposed adjacent to the collimator for converting X-rays to light energy, and photodiodes for receiving the light energy from the adjacent scintillator and producing electrical signals therefrom. An intensity of the attenuated beam radiation received at the detector array is typically dependent upon the attenuation of the X-ray beam by the patient. Each detector element of a detector array produces a separate electrical signal indicative of the attenuated beam received by each detector element. The electrical signals are transmitted to a data processing system for analysis. The data processing system processes the electrical signals to facilitate generation of an image.

The X-ray source includes an X-ray tube, where a cathode emits a beam of electrons directed towards an anode of the X-ray source, striking a target of the X-ray source. A size and shape of the focal spot may partially depend on an angle of a surface of the target with respect to the beam of electrons directed towards the anode. The size and shape of the focal spot on the target may be adjusted by focusing the electron beam via electrostatic controls, electromagnetic controls, or a combination of electrostatic and electromagnetic controls. X-rays emitted as a result of the electrons colliding with the target are focused on the patient at an effective focal spot based on the focal spot.

On the target, a focal spot may have a height corresponding to a Z dimension, where the Z dimension is aligned with a length of a body of the patient (e.g., from a head of the patient to the toes of the patient), and the focal spot may have a width corresponding to an X dimension, where the X dimension is aligned with a width of the body of the patient (e.g., from the patient's left side to the patient's right side). The height and width of the focal spot may be controlled by the electrostatic and/or electromagnetic controls used to focus the electron beam. Additionally, a distribution of electrons of the electron beam colliding with the target may be controlled by the electrostatic and/or electromagnetic controls. For example, the electrostatic and/or electromagnetic controls may be adjusted to generate a first focal spot with a first distribution of electrons having a first height and a first width, or the electrostatic and/or electromagnetic controls may be adjusted to generate a second focal spot with a second distribution of electrons having a second height and a second width, where one or more of the second distribution, second height, and second width are different from the first distribution, first height, and first width, respectively.

A position of the focal spot on the target may be adjusted via the electrostatic and/or electromagnetic controls. In other words, the focal spot may be deflected by either or both of the electrostatic and electromagnetic controls from a first position on the target to a second position on the target. For example, the focal spot may be deflected in the X dimension, where the first position is at a first X position, and the second position is at a second X position, or the focal spot may be deflected in the Z dimension, where the first position is at a first Z position, and the second position is at a second Z position, or the focal spot may be deflected in both the X dimension and the Z dimension. Further, the CT system may provide a "2-point", "wobble" or "flying focal spot" mode, where the focal spot may alternate between the first position and the second position in consecutive views acquired by the CT system. For example, a first image of a sequence of images may be generated from a first view, where the focal spot is at the first position. A second image of the sequence may be generated from a second view, where the focal spot is at the second position. A third image of the sequence may be generated from a third view, where the focal spot is at the first position, and a fourth image of the sequence may be generated from a fourth view, where the focal spot is at the second position, and so on. By deflecting the focal spot to alternate between the first position and the second position, a quality of the images generated may be increased.

A quality of an image generated by the X-ray detector array may depend on a size of the focal spot. When the focal spot is larger, more X-ray flux can be delivered to the patient, which allows imaging of thicker or higher-absorbing anatomy in a shorter time, or generally producing images with lower noise. When the focal spot is smaller, less X-ray flux is delivered to the patient, when using an X-ray tube where thermal properties of the target may constrain the tube current. However, when the focal spot is smaller, a spatial resolution of the image may be higher, and as the size of the focal spot increases, the spatial resolution of the image may decrease. Thus, a tradeoff exists between power (e.g., a number of electrons colliding with the target) and spatial resolution. For some clinical tasks, higher power may be desired for less image noise, while for other clinical tasks, a lower signal may be desired to reduce artifacts.

X-ray tubes can produce focal spots of different shapes and sizes to preset specifications. The tube focal spot is controlled by shaping an electron beam emitted by the cathode by means of electrostatic deflection or magnetic focusing. Control settings are typically adjusted on a real-time basis to keep the focal spot within specifications during an exposure. For mA modulated scans, this may involve adjusting electrode or magnet settings instantaneously during the exposure to produce a same size focal spot regardless of tube current. Focal spot size typically increases to support increased x-ray power output levels. Concentrating too much energy in a small spot can melt or damage the track on the x-ray tube target. Consistent with regulations for x-ray generation for medical CT, X-ray tubes are typically designed to produce a number of discrete focal spots that can be individually selected for a scan, rather than a continuously variable focal spot allowed to meet variable specifications during one exposure.

When selecting CT exposure parameters for mA modulated scans, the system usually chooses a smallest available spot (e.g., where available focal spot sizes are pre-defined focal spot sizes for the CT system) that supports the maximum instantaneous tube power used to produce the highest prescribed current without damage to the tube. A smaller focal spot may be preferable in order to maximize spatial resolution performance for the system. The focal spot size is then kept at the same specifications throughout the exposure, from beginning to end, while the tube cathode increases or decreases the instantaneous X-ray tube output flux by changing tube current from view to view for mA modulated scans.

One reason why focal spot specifications are kept constant throughout an exposure is to allow reconstructing images without artifacts from a single set of calibration vectors. Calibration vectors are usually specific to each supported focal spot, among other things. However, because mA modulated scans can span a wide range of currents from low current values to high current values, the tube and/or the CT system may have to be calibrated for a large range of currents for each supported focal spot. This can take time or increase a complexity of calibration procedures and storage space.

In addition, for desired mA modulation profiles that include high variation from low currents to high currents to better conform to a patient's anatomy, applying the largest focal spot size used for the highest current to the rest of the exposure may reduce the overall spatial resolution performance for the scan.

Methods and systems are therefore proposed herein for adjusting the size of a focal spot dynamically and purposefully during a continuous mA modulated CT exposure. The mA modulated profiles are usually precomputed before the X-ray exposure, based on a prior scan such as a scout image or a combination of scout images and a target radiation dose to be delivered to the patient or a target image quality to be achieved for the exam. The profile of the patient or scanned object, such as an oval ratio or a water-equivalent attenuation profile, is precomputed and used as an input to an AEC algorithm (Automated Exposure Control) that calculates the desired mA modulation profile to be applied during the CT exposure in order to meet certain characteristics such as radiation dose, noise, or uniformity targets, or a combination thereof. However, as described herein, for a given precomputed mA modulation profile, the focal spot size may be selected dynamically on a view-by-view basis rather than choosing the smallest focal spot required for the highest current in the scan and applying that same focal spot throughout the whole exposure (all the views). For each view, the smallest focal spot needed to support the current of that view is selected. When the X-ray exposure starts, the X-ray tube is commanded to produce the dynamic focal spots on a view-by-view basis during the exposure, where two consecutive views may have different specifications in terms of focal spot performance.

Figure 2:
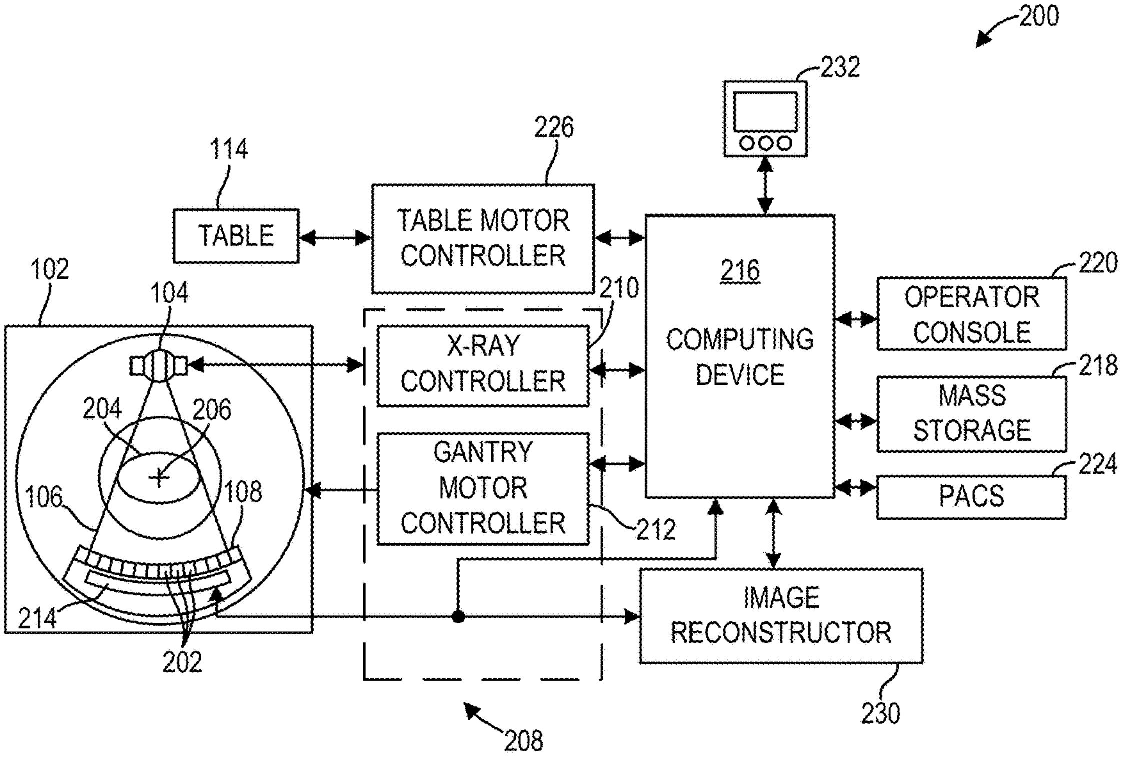
FIG. 2 shows a block schematic diagram of an exemplary imaging system, in accordance with one or more embodiments of the present disclosure.
Figure 4:
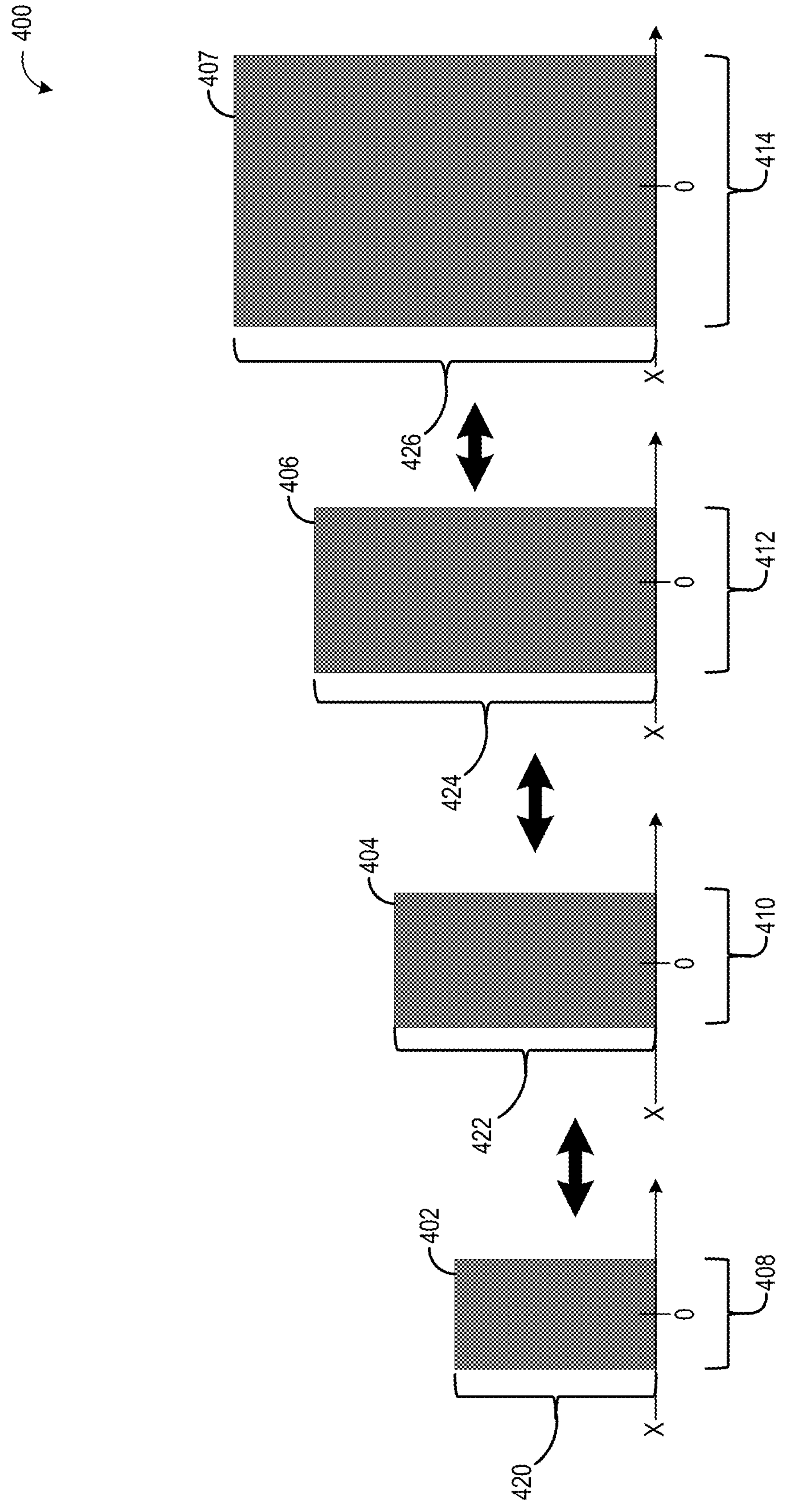
FIG. 4 shows a distribution of electrons of an electron beam of a CT system focused on four discrete focal spots, in accordance with one or more embodiments of the present disclosure.
Figure 5:
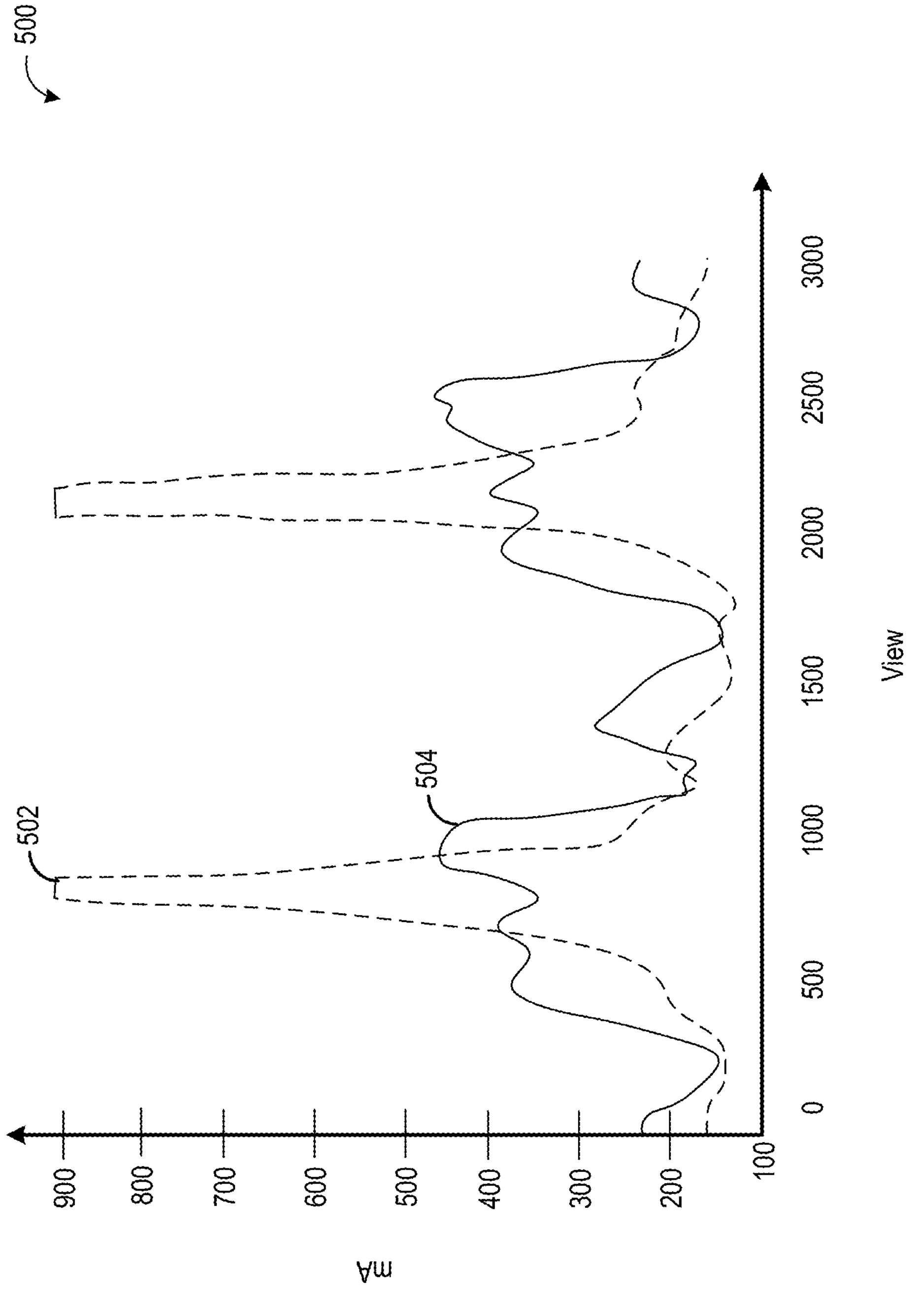
FIG. 5 shows a graph of two different exemplary mA modulation profiles precomputed for an object of interest to be scanned by a CT system using mA modulation.
Figure 6:
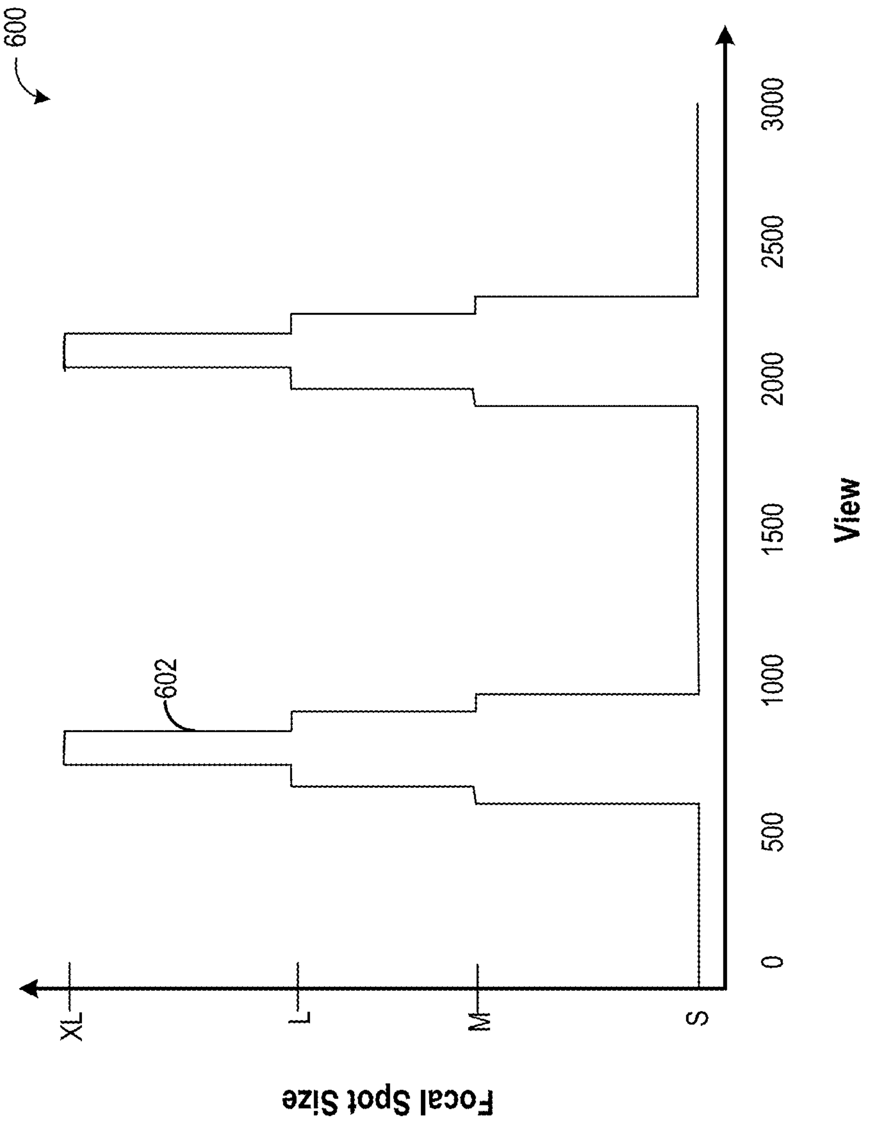
FIG. 6 shows a graphical depiction of dynamically resizing a focal spot for an aggressive mA modulation profile of FIG. 5, in accordance with one or more embodiments of the present disclosure.
Figure 7:
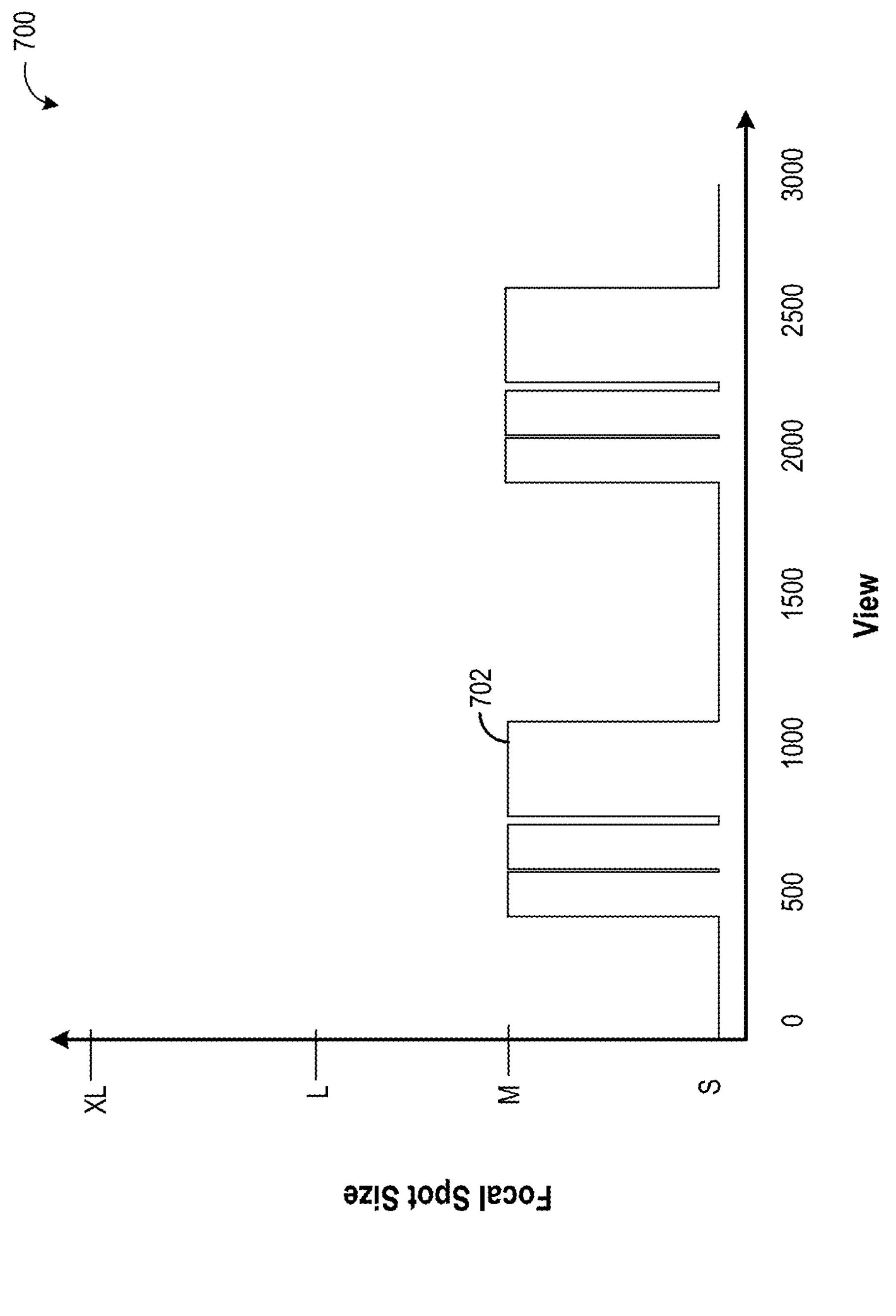
FIG. 7 shows a graphical depiction of dynamically resizing a focal spot for a less aggressive mA modulation profile of FIG. 5, in accordance with one or more embodiments of the present disclosure.

An example of a CT system that may be used to perform contrast scans in accordance with the present techniques is provided in FIGS. 1 and 2. FIG. 3A shows an example X-ray tube, where an electron beam is focused on a target at a composite focal spot, such as the composite focal spot shown in FIG. 3B. FIG. 4 shows four discrete focal spot sizes. FIG. 5 shows a graph of two different mA profiles precomputed for an object of interest to be scanned with modulated mA. For each mA profile, rather than applying the smallest available focal spot to all views, a smallest focal spot of a selection of supported focal spot sizes may be used for each view, as shown graphically in FIGS. 6 and 7, where FIG. 6 shows an aggressive mA modulation profile and FIG. 7 shows a less aggressive modulation profile. The size of the focal spot may be changed by following one or more steps of a method described in reference to FIG. 8.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging plane and around the object to be imaged such that an angle at which the X-ray beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

The X-ray source 104 includes an anode and a cathode. Electrons emitted by the cathode (e.g., resulting from energization of the cathode) may be intercepted by a target arranged at or near the anode. Electrons intercepted by the target may release energy in the form of X-rays, with the X-rays being directed toward the detector array 108. An area of the target surface that receives the electrons from the cathode and forms the emitted X-rays may be referred to herein as a focal spot. The emitted X-rays may be focused on a portion of the scanned subject 204, at an effective focal spot. A size of the effective focal spot may depend on an angle of the actual focal spot (e.g., on the target surface). For example, a small effective focal spot may be desirable when scanning a small area, while a large effective focal spot may be desirable when scanning a larger area. In some embodiments, an X-ray generation system including the X-ray source 104 may move and/or shape the focal spot. For example, the X-ray generation system may increase or decrease a size of the focal spot.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the X-ray radiation beam 106 (see FIG. 2) that pass through the subject 204 (such as a patient) to acquire corresponding projection data. In some embodiments, the detector array 108 may be fabricated in a multi-slice configuration including the plurality of rows of cells or detector elements 202, where one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage device 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Referring now to FIG. 3A, an exemplary X-ray tube 300 is shown. In one embodiment, the X-ray tube 300 may be the X-ray source 104 (see FIGS. 1-2). In the illustrated embodiment, the X-ray tube 300 includes an exemplary cathode 302 and an anode 303 disposed within a tube casing 306. The cathode may include one or more emitters 308. The one or more emitters 308 may be flat emitters, or curved emitters that are concave in curvature, providing pre-focusing of the electron beam. In other embodiments, a shaped emitter such as a square, rectangular, elliptical, or circular emitter may be employed. It may be noted that emitters of different shapes or sizes may be employed based on the application requirements. For example, in some embodiments, two emitters 308 may be used, where a first emitter 308 may generate a first focal spot on the target 304, and a second emitter 308 may generate a second focal spot on the target 304.

In the present example, the cathode 302, and in particular the one or more emitters 308, may be directly heated by passing a current through the one or more emitters 308, which may be supplied by a voltage source 310. In one embodiment, a current of about 10 amps (A) may be passed through the one or more emitters 308. The one or more emitters 308 may emit an electron beam 312 as a result of being heated by the current supplied by the voltage source 310. As used herein, the term "electron beam" may be used to refer to a stream of electrons that have substantially similar velocities.

The electron beam 312 may be directed towards a target 304 to produce X-rays 314. More particularly, the electron beam 312 may be accelerated from the emitter 308 towards the target 304 by applying a potential difference between the one or more emitters 308 and the anode 303. In one embodiment, a high voltage in a range from about 40 kV to about 450 kV may be applied to set up the potential difference between the one or more emitters 308 and the anode 303, thereby generating one or more electric fields 320 in the X-ray tube 300. In one embodiment, a high voltage differential of about 140 kV may be applied between the one or more emitters 308 and the anode 303 to accelerate the electrons in the electron beam 312 towards the target 304. As an example, the one or more emitters 308 may be at a potential of about −140 kV and the anode 303 and target 304 may be at ground potential or about zero volts.

The electron beam 312 may impinge on the target 304 at a focal spot 332. Focal spot 332 may have an orientation indicated by coordinate axes 349. When the electron beam 312 impinges upon the target 304, heat may be generated in the target 304 at a location of the focal spot 332, which may be significant enough to melt the target 304. In various embodiments, a rotating target may be used to circumvent the problem of heat generation in the target 304. For example, the target 304 may be configured to rotate such that the focal spot 332 generated by the electron beam 312 striking the target 304 does not strike the target 304 consistently at the same location, so that the target 304 may not melt. In various embodiments, the target 304 may include materials such as, but not limited to, tungsten or molybdenum.

Figure 3B:
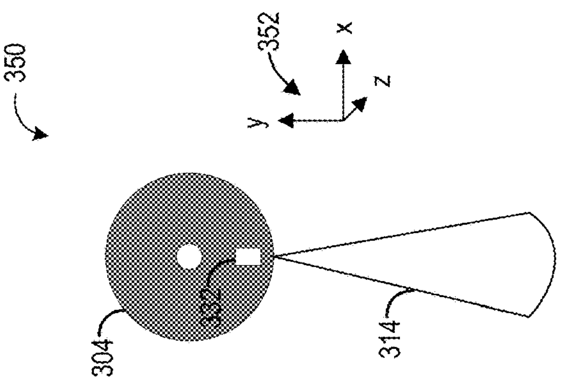
FIG. 3B is a schematic diagram of a focal spot on a target, in accordance with one or more embodiments of the present disclosure.
Figure 3A:
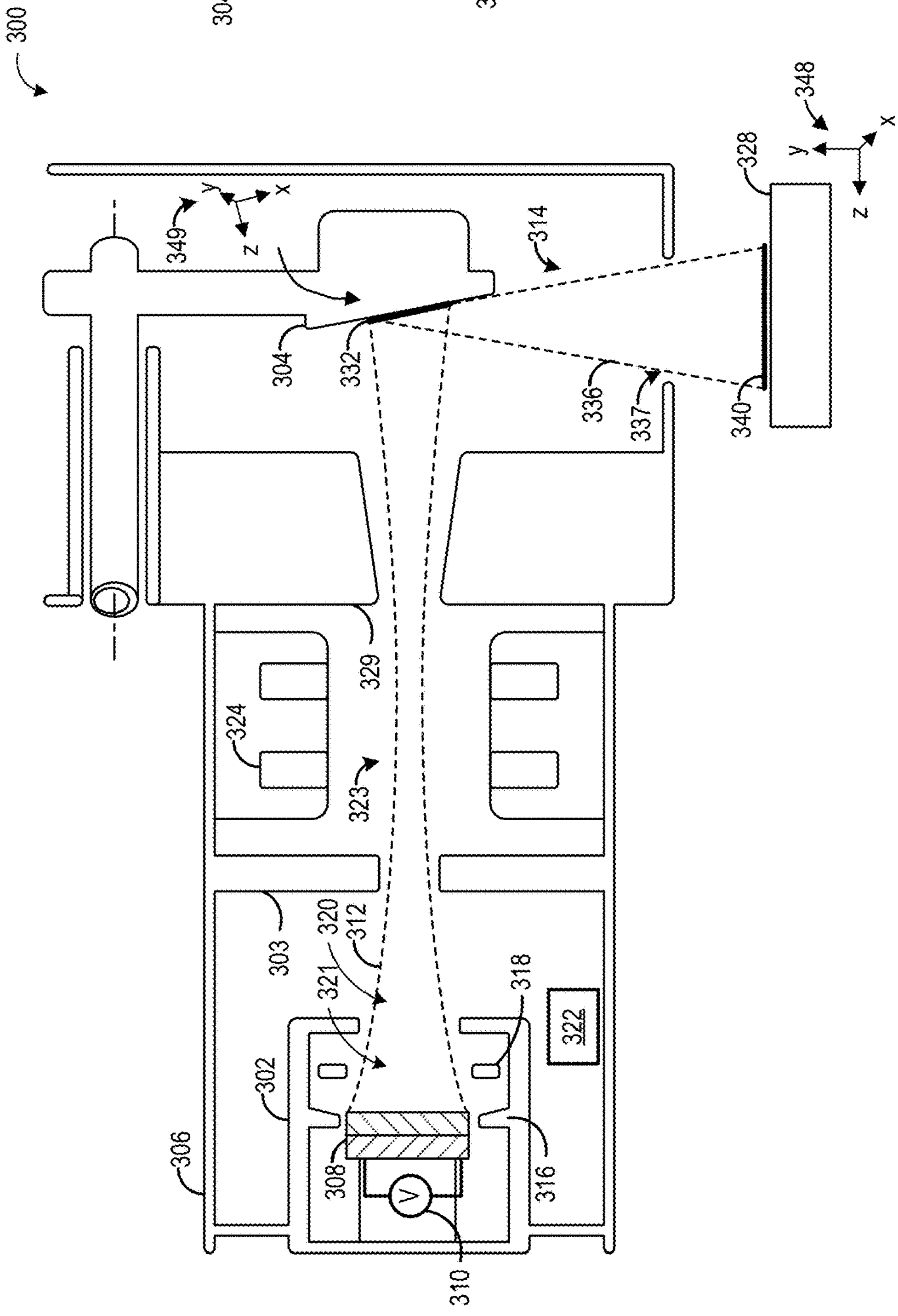
FIG. 3A is a schematic diagram of an exemplary X-ray tube, in accordance with one or more embodiments of the present disclosure.

Referring briefly to FIG. 3B, a front view 350 of the target 304 is shown, including the focal spot 332. Focal spot 332 may have an orientation in FIG. 3B indicated by coordinate axes 352. As described above, the target 304 may be a circular target that rotates such that the focal spot 332 is generated at different locations on a surface of the target 304 as the target 304 rotates. By generating the focal spot 332 at different locations on the surface of the target 304, an amount of heat absorbed at a location of the target 304 may be minimized.

Returning to FIG. 3A, size of a focal spot on the target 304 may also be adjusted to reduce an amount of heat generated in the target 304, where a smaller focal spot may generate a greater amount of heat at a specific location. An electron collector 329, held at a same potential as the target 304, serves as a sink of electrons that bounce off the surface of 304 during the initial impact, which reduces the chance of those same electrons re-striking the target. Collecting the backscattered electrons in this way further may reduce target heating.

The X-ray tube 300 may include one or more focusing electrodes 316, which may be disposed adjacent to the emitter 308 such that the one or more focusing electrodes 316 focus the electron beam 312 towards the target 304. As used herein, the term "adjacent" means near to in space or position. To focus the electron beam 312, voltages may be applied to the one or more focusing electrodes 316 to generate the one or more electric fields 321. The voltages may be different for each of the one or more focusing electrodes 316. For example, a first voltage may be applied to a first focusing electrode 316; a second voltage may be applied to a second focusing electrode 316; a third voltage may be applied to a third focusing electrode 316; and so on. For some focusing electrodes 316, the voltage may be 0, where no voltage is applied to the focusing electrode 316. In some embodiments, a first portion of the focusing electrodes 316 may be used for deflecting the electron beam 312, and a second portion of the focusing electrodes 316 may be used for focusing the electron beam 312. In this way, the voltages may be selectively applied by a controller of a control electronics module 322 to generate one or more specific electric fields that focus the electron beam 312 to a desired shape and deflect the electron beam 312 to a desired position.

In some embodiments, the one or more focusing electrodes 316 may each be maintained at a voltage potential that is less than a voltage potential of the one or more emitters 308. The potential difference between the one or more emitters 308 and the one or more focusing electrodes 316 may prevent electrons generated from the one or more emitters 308 from moving towards the one or more focusing electrodes 316. In some embodiments, the one or more focusing electrodes 316 may be maintained at a negative potential with respect to that of the one or more emitters 308. The negative potential of the one or more focusing electrodes 316 with respect to the one or more emitters 308 may focus the electron beam 312 away from the one or more focusing electrodes 316, thereby facilitating focusing of the electron beam 312 towards the target 304.

In other embodiments, the one or more focusing electrodes 316 may be maintained at a voltage potential that is equal to or substantially similar to the voltage potential of the one or more emitters 308. The similar voltage potential of the one or more focusing electrodes 316 with respect to the voltage potential of the one or more emitters 308 may create a parallel electron beam by shaping electrostatic fields due to the shape of the one or more focusing electrodes 316. The one or more focusing electrodes 316 may be maintained at a voltage potential that is equal to or substantially similar to the voltage potential of the one or more emitters 308 via use of a lead coupling the emitter 308 and the one or more focusing electrodes 316.

Additionally, the X-ray tube 300 may include one or more extraction electrodes 318, which may be used for additionally controlling and focusing the electron beam 312 towards the anode 303. The one or more extraction electrodes 318 may be located between the anode 303 and the one or more emitters 308. In some embodiments, the one or more extraction electrodes 318 may be positively biased by supplying a desired voltage to the one or more extraction electrodes 318.

An energy of the electron beam 312 may be controlled in various ways. For instance, the energy the electron beam 312 may be controlled by altering the potential difference (e.g., an acceleration voltage) between the cathode 302 and the anode 303. As used herein, the term "electron beam current" refers to a flow of electrons per second between the cathode 302 and the anode 303. The current of the electron beam 312 may be controlled by adjusting the emitter voltage 310 to change the temperature of the emitter 308. The electron beam current may be controlled by altering the voltage applied to the one or more extraction electrodes 318. It may be noted that the one or more emitters 308 may be treated as an infinite source of electrons.

The one or more electric fields 321 may be generated between the one or more extraction electrodes 318 and the one or more focusing electrodes 316 due to a potential difference between the one or more focusing electrodes 316 and the one or more extraction electrodes 318. A strength of the one or more electric fields 320 may be employed to control the intensity of electron beam 312 generated by the one or more emitters 308 towards the anode 303. More particularly, the one or more electric fields 320 may cause the electrons emitted by the one or more emitters 308 to be accelerated towards the anode 303. The stronger the one or more electric fields 320, the stronger the acceleration of the electrons from the one or more emitters 308 towards the anode 303. Alternatively, the weaker the one or more electric fields 320, the lesser the acceleration of electrons from the one or more emitters 308 towards the anode 303. The intensity of the electron beam 312 striking the target 304 may thus be controlled by the one or more electric fields 320 and 321.

Furthermore, voltage shifts of 8 kV or less may be applied to the one or more extraction electrodes 318 to control the intensity of the electron beam 312. In certain embodiments, these voltage shifts may be applied to the one or more extraction electrodes 318 via use of the control electronics module 322. The control electronics module 322 may be a non-limiting embodiment of, or may be a part of X-ray controller 210 of FIG. 2.

As the electron beam 312 is focused on the target 304, the electrons may form a Gaussian distribution. For the purposes of this disclosure, the Gaussian distribution may be an approximately Gaussian distribution. The Gaussian distribution of electrons of the electron beam 312 may be narrowed or parallelized, where electrons colliding with the target 304 at sides of the Gaussian distribution may be directed towards a center of the Gaussian distribution. Said a different way, a distribution of electrons at the sides of the Gaussian distribution may be inverted, resulting in a focal spot of a rectangular shape or batwing shape.

Additionally, the X-ray tube 300 may also include a one or more magnets 324 for focusing and/or positioning and deflecting the electron beam 312 onto the target 304. In various embodiments, the one or more magnets 324 may be disposed between the cathode 302 and the target 304. In some embodiments, the one or more magnets 324 may include one or more multipole magnets for influencing focusing of the electron beam 312 by creating one or more magnetic fields 323 that shapes the electron beam 312 on the target 304. The one or more multipole magnets may include one or more quadrupole magnets, one or more dipole magnets, or combinations thereof. For example, dipole magnets may be used to deflect the electron beam 312, positioning the electron beam 312 in a first dimension, while quadrupole magnets may be used to focus the electron beam 312 in two dimensions (e.g., a length and a width of the electron beam 312). For example, in a first step, the electron beam generated by the one or more emitters 308 may be deflected and focused by electrostatic focusing. In a second step, the electron beam may be further deflected by the one or more dipole magnets, to adjust a position of a focal spot of the electron beam on the target 304. In a third step, which may occur before or after the second step, the electron beam may be focused to generate a desired distribution of electrons on the target (e.g., a desired shape of the focal spot).

As properties of the electron beam current and voltage change, electrostatic focusing of the electron beam 312 will change accordingly. In order to maintain a stable size, shape, and other characteristics of a focal spot, or quickly modify focal spot size and/or shape according to system requirements, the one or more magnets 324 may provide a magnetic field having a performance controllable from steady-state to a sub-30 microsecond time scale for a wide range of focal spot sizes and shapes. When the electron beam 312 has been focused and positioned, the electron beam 312 impinges upon the target 304 at a focal spot 332 to generate the X-rays 314. The X-rays 314 generated by collision of the electron beam 312 with the target 304 may be directed from the X-ray tube 300 through an opening in the tube casing 306, at an X-ray window 337, towards an object 328.

As a result of the electron beam 312 colliding with target 304 at the focal spot 332, a set of X-rays 336 may be generated and directed out X-ray window 337 towards the object 328. The set of X-rays 336 may intersect with the object 328 at an effective focal spot 340. The effective focal spot may have a width (in an X dimension, as indicated by coordinate axes 348) and a length (in an Z dimension, as indicated by the coordinate axes 348).

As described above, X-ray tubes may be designed to produce a number of discrete focal spots that can be individually selected for a scan. In other words, the CT system may be configured to focus electron beam 312 to generate a single focal spot to be used for all views of the scan. However, as described in greater detail in FIGS. 4-9, the electron beam 312 may also be electrostatically and/or magnetically controlled and focused dynamically, to adjust the size of the focal spot between views of a CT scan. Specifically, different focal spots of the number of discrete focal spots may be selected for different portions of views of the CT scan.

For example, the CT system may support four different focal spot sizes: a small focal spot, a medium focal spot, a large focal spot, and an extra-large focal spot. As described herein, a first focal spot size may be selected for a first portion of the views, where the first focal spot size may be based on a first range of currents applied to the emitters 308 of the CT system; a second focal spot size may be selected for a second portion of the views, where the second focal spot size may be based on a second range of currents applied to the emitters 308 of the CT system, where the second range is different from the first range; and so on. If the first range of currents includes high level currents, the first focal spot may be large. If the second range of currents includes lower level currents than the first range, the second focal spot may be smaller than the first focal spot. By dynamically adjusting the size of the focal spot between portions of views (e.g., by selecting different sized focal spots for portions with different current ranges), a spatial resolution of images reconstructed using the differently-sized focal spots may be higher than a spatial resolution of images reconstructed using a single, large focal spot covering the maximum tube current range for all views.

Referring now to FIG. 4, a diagram 400 shows a distribution of electrons of an electron beam (e.g., electron beam 312) of a CT system focused on a first focal spot 402 of a first size, a second focal spot 404 of a second size, a third focal spot 406 of a third size, and a fourth focal spot 407 of a fourth size, which may each be the same as or similar to the focal spot 332 of FIG. 3A on the target 304. In various embodiments, the focal spots 402, 404, 406, and 407 may be examples of discrete focal spot sizes supported by the CT system, where other focal spot sizes may not be supported by the CT system.

A size and shape of the focal spots 402, 404, 406, and 407 may depend on one or more electric fields or electromagnetic fields (e.g., the one or more electric fields 321) generated by one or more focusing electrodes (e.g., the one or more focusing electrodes 316). For example, the one or more electric fields may perform a first focusing of an electron beam (e.g., electron beam 312) to generate the first focal spot 402. The one or more electric fields may perform a second focusing of the electron beam to generate the second focal spot 404. The one or more electric fields may perform a third focusing of the electron beam to generate the third focal spot 406. The one or more electric fields may perform a fourth focusing of the electron beam to generate the fourth focal spot 406. In some embodiments, size and shape of the focal spots 402, 404, 406, and 407 may also depend on one or more magnetic fields (e.g., the magnetic fields 323) generated by one or more magnets (e.g., the one or more magnets 324), which may further focus the electron beam after focusing is performed by the one or more electric fields.

The distributions of electrons generating the focal spots 402, 404, 406, and 407 are depicted as having a shape that is rectangular. While the rectangular shape may be approximated on the target as a result of a configuration of the one or more electric fields, the one or more magnetic fields, and various shields or barriers of the CT system, it should be appreciated that the distribution of electrons throughout the focal spots may not be uniform, but rather based on combinations of distributions generated by the configuration of the one or more electric fields and/or the one or more magnetic fields.

The first focal spot 402 has a length 420 and a width 408, as measured along an X-axis of the first focal spot 402. Thus, the first focal spot 402 has a first size based on the length 420 and the width 408. The second focal spot 404 may have a different length 422, and have a different width 410. In FIG. 4, width 410 is greater than width 408 and length 422 is greater than length 420, but in other examples, width 410 may be less than width 408 and/or length 422 may be less than length 420, whereby second focal spot 404 may have a smaller size than first focal spot 402. Similarly, the third focal spot 406 and fourth focal spot 407 may each have different widths 412 and 414, respectively, and lengths 424 and 426, respectively, which may be greater or less than either or both of widths 408 and 410 and/or lengths 420 and 422. In some embodiments, any of lengths 420-426 may be the same as other lengths 420-426, and/or any of widths 408-414 may be the same as other widths 408-414.

The size of the focal spots 402, 404, 406, and 407 may be dynamically adjusted in various ways. As an emitter is activated with a predetermined amount of current (e.g., as prescribed by an mA modulation strategy), a first amount of energy (e.g., current) delivered to the one or more focusing electrodes and a second amount of energy delivered to the one or more magnets may each be independently controlled to focus the electron beam on the target to achieve a desired size.

The emitter may include a filament with a coil diameter. An amount of power generated by the emitter may depend on the coil diameter. For example, if the coil diameter is larger, a greater amount of power (e.g. a greater number of electrons) may be generated by the emitter. If the coil diameter is smaller, less power may be generated by the emitter. A shape of the focal spots 402, 404, 406, and 407 may be based on a shape of the emitter. For example, the emitter may be flat, which may generate a first electron distribution, or the emitter may be curved, which may generate a second, different electron distribution. As a result of the different emitter shapes, a shape of the focal spot may be different. Additionally, as described above with respect to the coil diameters, a flat emitter may have a large emission area, generating a greater amount of power (e.g. a greater number of electrons) and creating a larger (e.g., wider) focal spot, or the flat emitter may have a smaller emission area, generating a lesser amount of power (e.g. a lesser number of electrons) and creating a smaller (e.g., narrower) focal spot.

The focusing electrodes and the magnets may be activated to dynamically switch between the first focal spot 402, the second focal spot 404, the third focal spot 406, and the fourth focal spot 407 during an exposure. The electron beam may be focused on the target with first focal spot 402 for a first duration; the electron beam may be focused on the target with second focal spot 404 for a second duration; the electron beam may be focused on the target with third focal spot 406 for a third duration; and the electron beam may be focused on the target with fourth focal spot 407 for a fourth duration. The first duration, the second duration, the third duration, and the fourth duration may all be the same, or the first duration, the second duration, the third duration, and the fourth duration may all be different, or one or more of the first duration, the second duration, the third duration and the fourth duration may be the same.

The electron beam may transition from the first duration to the second duration continuously without a break in imaging/scanning. In other words, dynamically switching between focal spots 402, 404, 406, and 407 may refer to modulating the focal spot size during a continuous X-ray exposure (e.g., between x-ray on and x-ray off), rather than fixing the size of a focal spot during a sub-exposure and switching the X-ray off to perform an adjustment of focal spot size or a selection of a different focal spot size as may be performed in other types of CT scans. By adjusting the size of the focal spot during the exposure, an overall spatial resolution of reconstructed images may be increased, producing higher quality images without generating artifacts. Additionally, if the detector is sensitive to the photon count rate, eliminating overlaps in mA ranges and focal spot combinations can reduce the overall system calibration space.

An order of the focal spots may also vary. For example, for a first exposure, first focal spot 402 may be followed by second focal spot 404; second focal spot 404 may be followed by third focal spot 406; and third focal spot may be followed by second focal spot 404. For a second exposure, first focal spot 402 may be followed by second focal spot 404; second focal spot 404 may be followed by first focal spot 402; and first focal spot 402 may be followed by second focal spot 404. Thus, focal spot size may be increased or decreased over an exposure. It should be appreciated that the examples provided herein are for illustrative purposes, and focal spots of varying sizes may be used in different orders without departing from the scope of this disclosure.

The first duration may correspond to a first portion of a total number of views of the CT scan; the second duration may correspond to a second portion of a total number of views; the third duration may correspond to a third portion of a total number of views; and the fourth duration may correspond to a fourth portion of a total number of views. In various embodiments, the first, second, third, and fourth portions of the views may be selected based on an amount of current applied at different times during the scan, in accordance with an mA modulation profile. For example, during the first portion of the views, a first amount of current may be applied, where the first amount of current is within a first range of current values. The size of first focal spot 402 may be based on the first amount of current. During the second portion of the views, a second amount of current may be applied, where the second amount of current is within a second range of current values. The size of second focal spot 404 may be based on the second amount of current. During the third portion of the views, a third amount of current may be applied, where the third amount of current is within a third range of current values. The size of third focal spot 406 may be based on the third amount of current. During the fourth portion of the views, a fourth amount of current may be applied, where the fourth amount of current is within a fourth range of current values. The size of fourth focal spot 406 may be based on the fourth amount of current.

In other words, when an amount of current applied to the cathode at a view is the same as an amount of current applied to the cathode at an immediately preceding view, the view and the preceding view may be within a same portion of the views, whereby a size of a focal spot selected for the view may be the same as a size of a focal spot selected for the immediately preceding view. Alternatively, when the amount of current applied to the cathode at the view is different from the amount of current applied to the cathode at the immediately preceding view, the view and the preceding view may not be within a same portion of the views, whereby the size of the focal spot selected for the view may be different from the size of the focal spot selected for the immediately preceding view.

For example, the first range of current values may be between 0 and 360 mA; the second range of current values may be between 360 mA and 515 mA; the third range of current values may be between 515 mA and 765 mA; and the fourth range of current values may be between 765 mA and 900 mA. Thus, if a current applied during the CT scan varies between 0 mA and 900 mA, the total number of views of the CT scan may be divided into the first portion, the second portion, the third portion, and the fourth portion based on the corresponding current value ranges. In other words, in response to a current applied to the emitter being between 0 and 360 mA, the one or more electric fields and the one or more magnetic fields may be configured in a first configuration for the first duration to generate the first focal spot 402. In response to the current applied to the emitter being between 360 mA and 515 mA, the one or more electric fields and the one or more magnetic fields may be configured in a second configuration for the second duration to generate the second focal spot 404. In response to the current applied to the emitter being between 515 mA and 765 mA, the one or more electric fields and the one or more magnetic fields may be configured in a third configuration for the third duration to generate the third focal spot 406. In response to the current applied to the emitter being between 765 mA and 900 mA, the one or more electric fields and the one or more magnetic fields may be configured in a fourth configuration for the fourth duration to generate the fourth focal spot 407.

In some embodiments, the ranges may not be mutually exclusive, and may overlap. For example, in addition to an amount of current, the size of a focal spot may be selected based on current and additional criteria, such as, for example, an anatomical region of a subject, an attenuation path length through a scanned object, or a view angle, or a different criterion. If the amount of current is within two overlapping current ranges, either a focal spot size corresponding to a first range of the two overlapping current ranges may be selected, or a focal spot size corresponding to a second range of the two overlapping current ranges may be selected, based on the additional criteria. In some embodiments, a large focal spot may be used with overlapping ranges (e.g., for example in a scout scan), even for low mA scans. In these cases, the spatial resolution requirements of the scan is not high and a large spot may result in more efficient thermal management of the X-ray tube.

In some cases, the total number of views may be divided into a small number of portions (e.g., such as four portions). For example, in accordance with the mA modulation profile, the amount of current applied during the scan may remain within the first range of current values for a first plurality of views, where the focal spot 402 may be used on the first plurality of views. The amount of current applied may change from being within the first range of current values to being within the second range of current values, and may remain within the second range of current values for a second plurality of views, where the focal spot 404 may be used on the second plurality of views. The amount of current applied may change from being within the second range of current values to being within the third range of current values, and may remain within the third range of current values for a third plurality of views, where the focal spot 406 may be used on the third plurality of views. The amount of current applied may change from being within the third range of current values to being within the fourth range of current values, and may remain within the fourth range of current values for a fourth plurality of views, where the focal spot 407 may be used on the fourth plurality of views.

However, in other cases, the amount of current applied during the scan may vary more frequently between views and with larger changes, where the size of the focal spot may change more frequently. In other words, in some examples, any of the first, second, third, and/or fourth portion of views may comprise one or a small number of views. For example, the focal spot 402 may be used in a first view; the focal spot 404 may be used in a subsequent second view; the focal spot 402 may be used in a subsequent third view; the focal spot 406 may be used in a subsequent fourth view; and so on, where different focal spot sizes may be used for consecutive views or small groups of consecutive views.

In various embodiments, the size of a focal spot to be used in a view may be selected to be a smallest size possible for a given amount of current that does not exceed a power limit for an amount of concentrated energy within the focal spot on the target. Thus, as the amount of current increases in accordance with the mA modulation, larger sized focal spots may be selected. As the amount of current decreases, smaller sized focal spots may be selected. In this way, degradation of the target and/or X-ray tube may be averted.

In other embodiments, the size of a focal spot to be used in a view may not be based on, or entirely based on the amount of current applied in accordance with the mA modulation, and the size of the focal spot may be selected at least partly based on other factors. For example, in one embodiment, a focal spot size may be selected based at least partly on a specific portion of an anatomy of a subject being scanned by the CT system, or based at least partly on a view angle of the projection view. For example, at a first view angle, the electron beam may pass through a small portion of a body of a subject. In response to the electron beam passing through the small portion at the first view angle, a focal spot with a first size may be selected. At a second view angle, the electron beam may pass through a larger portion of the body of the subject. In response to the electron beam passing through the larger portion at the second view angle, a focal spot with a second size may be selected, where the second size may be smaller than the first size. For example, projection data from the first view angle may not include an anatomical region of interest of the subject, and projection data from the second view angle may include the anatomical region of interest. As a result of the projection data from the second view angle including the region of interest, a smaller focal spot may be used during the second view angle to increase a spatial resolution of an image acquired of the region of interest.

For example, a continuous helical scan may be performed covering multiple organs. For some organs, high spatial resolution may be desired for quality, while for other organs, high spatial resolution may not be desired for quality. In such a scenario, it could be better to choose a largest focal spot that meets the CTQs for each anatomy to optimize spatial resolution performance throughout the scanned region and x-ray tube thermal management.

One reason why focal spot size is typically kept constant throughout an exposure is to allow for reconstructing images without artifacts from a single set of calibration vectors. Calibration vectors are usually specific to each supported focal spot, among other things. However, because mA modulated scans can span a wide range of currents, the tube and/or the CT system may have to be calibrated for a large range of currents for each supported focal spot. This can take time and/or increase a complexity of calibration procedures and storage space. One advantage of selecting different focal spot sizes for different portions of projection views is that when projection view data is corrected, different calibration vectors may be used to correct the different portions of the projection views. For example, a first portion of projection view data may be corrected using a first calibration vector, where the first calibration vector may be selected based on the focal spot of the first size; and a second portion of projection view data may be corrected using a second calibration vector, the second calibration vector selected based on the focal spot of the second size. Using different calibration vectors may reduce X-ray tube and/or system calibration complexity, by creating a one-to-one mapping between focal spot size and current level for a given kV. In other words, rather than having to calibrate all focal spot sizes for a wide range of currents, each focal spot may be calibrated for a corresponding smaller specific current range, and not calibrated for other current ranges, thereby saving time and storage space.

For example, a supported minimum tube mA may be 10 mA, and a maximum supported tube mA may be 1300 mA. When a fixed size focal spot is used, to cover a full range of exposures that the system is capable of, for each kV, the tube should be able to produce focal spots in specs for the full range of currents used during mA modulation: [10, 360] mA for the S spot; [10, 515] mA for the M spot; [10, 765] mA for the L spot; [10, 1300] mA for the XL spot. However, when different focal spot sizes are used for different portions of a total number of views, the tube can be set up to produce focal spots in specs for a reduced range of currents: [10, 360] mA for the S spot (no change); [365, 515] mA for the M spot; [520, 765] mA for the L spot, and [770, 1300 mA] for the XL spot, where, for example, the current is available in increments of 5 mA. As a result, an overall calibration complexity may be substantially reduced (e.g., up to or more than 50%). This may also reduce calibration time by the same amount, or reduce calibration storage requirements (especially if the system requires mA-dependent calibrations), or increase overall tube life by reducing a number of X-ray on exposures required for calibrations vs. patient scanning. However, a complexity of calibration data management for processing may be increased by relying on multiple calibration vectors to reconstruct images without artifacts, where the calibration vectors are focal spot size specific.

Referring now to FIG. 5, a graph 500 shows two different exemplary mA modulation profiles precomputed for an object of interest to be scanned by a CT system using mA modulation, in a single rotation around the object and 3000 views per rotation. The 3000 views are depicted along an x axis of graph 500, and an amount of current applied during the CT scan to generate an electric beam is shown along a y axis of graph 500. Graph 500 includes two plots: a first mA modulation profile 502, and a second mA modulation profile 504.

First mA modulation profile 502 is an aggressive mA modulation profile, where a current applied in accordance with the mA modulation varies over a wide range of current values. First mA modulation profile 502 may be based on an object attenuation profile as a function of view angle on the x axis. With an objective of producing uniform noise in acquired data or reconstructed images, a greater current may be used for a longer attenuation path length through the object at a given view angle, whereas a smaller current may be used for a shorter attenuation path length through the object. For mA modulation profile 502, the current ranges from about 50 mA (e.g., a lowest amount of current) to 900 mA (e.g., a highest amount of current), where the profile is capped.

In comparison with first mA modulation profile 502, second mA modulation profile 504 is a less aggressive mA modulation profile. In second mA modulation profile 504, the current ranges from a minimum of about 60 mA to a maximum of about 460 mA, with peaks that are lower and broader than first mA modulation profile, which is characterized by higher and narrower peaks. Both first mA modulation profile 502 and second mA modulation profile 504 could be generated to produce a same overall radiation dose. However, images reconstructed from first mA modulation profile 502 may have a different performance in terms of noise distribution than images reconstructed from second mA modulation profile 504.

An X-ray tube of a CT system (e.g., CT system 100 and/or imaging system 200 of FIGS. 1 and 2, respectively) performing the CT scan may be capable of producing a number of discrete focal spots, where not all focal spot sizes may be allowed. For example, the X-ray tube may be capable of producing four discrete focal spots, each with different size and maximum power limits. For example, the four discrete focal spots may include a small spot (S) capable of a maximum of 360 mA; a medium spot (M) capable of a maximum of 515 mA; a large spot (L) capable of a maximum of 765 mA; an extra-large spot (XL) capable of at least 900 mA.

Typically, a fixed focal spot size would be used throughout a whole exposure commanded to the tube/generator for each of first mA modulation profile 502 and second mA modulation profile 504, where the fixed focal spot size is the smallest available focal spot that supports the maximum instantaneous tube power used to produce the highest prescribed current, without damage to the tube. Because the highest prescribed current of first mA modulation profile 502 exceeds 900 mA, the smallest available focal spot to support first mA modulation profile 502 would be the XL spot. Thus, the XL spot would be applied to all views. Because the highest prescribed current of second mA modulation profile 504 is approximately 450 mA, the smallest available focal spot to support second mA modulation profile 504 would be the M spot, which would also be applied to all views.

However, the smallest available focal spot that supports the maximum instantaneous tube power used to produce the highest prescribed current for an mA modulation profile may not be ideal for reconstructing images from lower-current views. In other words, the images from lower-current views may not have a desired spatial resolution. This may be particularly true for aggressive mA modulation profiles like first mA modulation profile 502, which have a wide range of currents.

As described above in reference to FIG. 4, the spatial resolution of images reconstructed from first mA modulation profile 502 and second mA modulation profile 504 may be increased by adjusting a size of a focal spot used for a given view based on one or more factors, such as an amount of current applied. For example, as the amount of current increases, a larger focal spot may be used, and as the amount of current decreases, a smaller focal spot may be used. Additionally, because of a difference in the range of currents used in first mA modulation profile 502 and the range of currents used in second mA modulation profile 504, a different selection of focal spot sizes may be used for first mA modulation profile 502 than for second mA modulation profile 504. FIGS. 6 and 7 show exemplary focal spot selections for first mA modulation profile 502 and second mA modulation profile 504, respectively.

Referring to FIG. 6, a graph 600 illustrates an exemplary set of focal spot sizes that may be selected to increase a spatial resolution of images reconstructed from a CT scan using mA modulation with the first mA modulation profile 502 of FIG. 5. The x axis of graph 600 is the same as for graph 500, showing the 3000 views of the CT scan. The y axis of graph 600 shows the different focal spot sizes described in reference to FIG. 5. Graph 600 includes a single plot 602, which indicates a size of a focal spot selected for each view of the 3000 views. Note that for fixed generator voltages, higher tube power may be equivalent to higher tube current. It should be appreciated that these values are chosen for the sake of illustration, and other values may be used without departing from the scope of this disclosure.

At each vertical transition of graph 600, the focal spot may change from one setting to another, then remain fixed until a next transition, creating a piecewise constant focal spot modulation profile during the mA-modulated exposure. For example, from view 0 to approximately view 650, the small focal spot may be selected, due to the current being applied during those views being less than 360 mA (e.g., as shown in graph 500 of FIG. 5). From approximately view 700 to approximately view 750, the medium focal spot may be selected, due to the current being applied during those views being between 360 mA and 515 mA. From approximately view 750 to approximately view 800, the large focal spot may be selected, due to the current being applied during those views being between 515 mA and 760 mA, and so on.

Referring now to FIG. 7, a graph 700 illustrates an exemplary set of focal spot sizes that may be selected to increase a spatial resolution of images reconstructed from a CT scan using mA modulation with the second mA modulation profile 504 of FIG. 5. The x axis of graph 700 is the same as for graph 500, showing the 3000 views of the CT scan. The y axis of graph 700 shows the different focal spot sizes. Graph 700 includes a single plot 702, which indicates a size of a focal spot selected for each view of the 3000 views.

For the second mA modulation profile 504, the CT system might use the small and medium spots, due to the current being applied during those views being less than 515 mA (e.g., as shown in graph 500 of FIG. 5). In other words, from view 0 to approximately view 450, the small focal spot may be selected, due to the current being applied during those views being less than 360 mA; from approximately view 450 to approximately view 550, the medium focal spot may be selected, due to the current being applied during those views being between 360 mA and 515 mA; and so on. Generally, the less aggressive second mA modulation profile 504 uses smaller focal spots than the more aggressive first mA modulation profile 502. However, both scenarios use small and medium spots when the current is low enough, and a small portion of the overall views use the larger focal spots.

Compared to exposures with fixed focal spot size throughout the exposure, modulating the focal spot size during the exposure provides various benefits. One of the benefits is that a significant portion of the exposure may be acquired at a smaller focal spot compared to using a consistently larger spot size throughout. Smaller focal spots may produce higher resolution images. When data is generated where a relatively small portion of the overall views use larger spot sizes, a preservation of high frequency details from the object may be increased. In the projection domain, spatial resolution may vary from view to view, leading to non-isotropic resolution in reconstructed images. However, when smaller spot sizes can be used, less blurring of edges perpendicular to the views may occur in comparison with using a fixed large focal spot, which may result in blurring edges consistently across all view angles. As a result, a higher resolution image overall may be generated. Higher spatial resolution allows visualizing smaller details of a scanned object or patient's anatomy.

Figure 8:
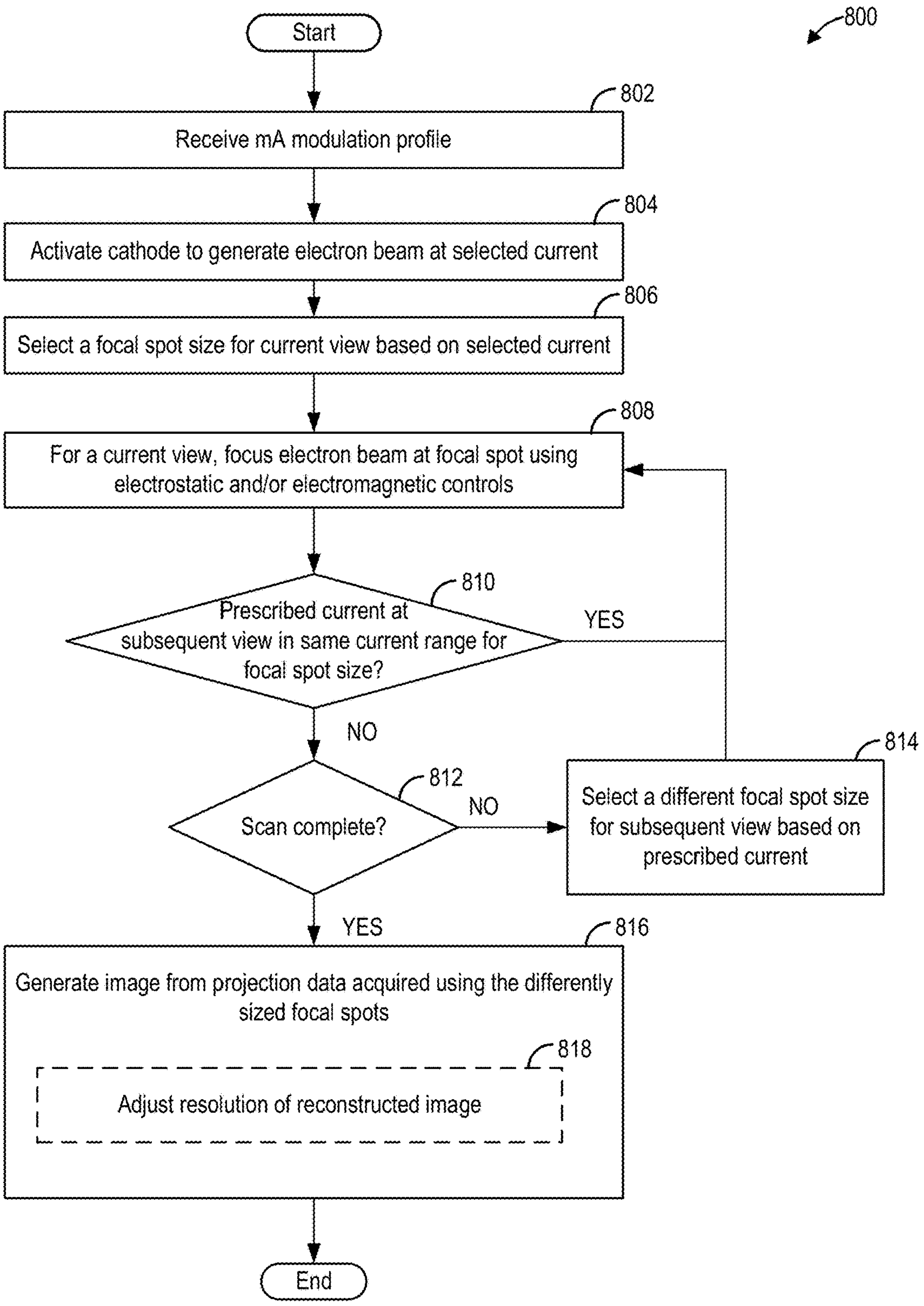
FIG. 8 is a flowchart illustrating an exemplary method for adjusting a size of a focal spot during a CT scan, in accordance with one or more embodiments of the present disclosure.

Referring now to FIG. 8, an example method 800 is shown for adjusting a size of a focal spot generated by a CT system during a CT scan of an object. Method 800 is described in reference to the CT system 100 of FIG. 1 and/or the imaging system 200 of FIG. 2. Method 900 may be executed by a processor of a controller of the CT system, such as processor of control electronics module 322 of FIG. 3A, in response to instructions provided by an operator of the CT system and/or stored in a memory of the CT system.

Method 800 begins at 802, where method 800 includes receiving an mA modulation profile from an Automatic Exposure Control (AEC) system of the CT system. The mA modulation profile may be precomputed before an X-ray exposure, based on a prior scan such as a scout image or a combination of scout images. A profile of the patient or scanned object, such as an oval ratio or a water-equivalent attenuation profile, may be precomputed and used as an input to an AEC algorithm that calculates the desired mA modulation profile to be applied during the CT exposure in order to meet certain characteristics such as radiation dose, noise, or uniformity targets, or a combination thereof.

At 804, method 800 includes activating a cathode of the CT system to generate an electron beam, as described above in reference to the electron beam 312 of FIG. 3A. The electron beam may be directed towards a target (e.g., target 304) of the CT system, where electrons of the electron beam may collide with the target to generate X-rays that may be directed at the object (e.g., object 328).

At 806, method 800 includes selecting a focal spot size for a current view (e.g., view angle) of the CT scan. The focal spot size may be selected from a plurality of pre-configured focal spot sizes supported by the CT system. For example, four different focal spot sizes may be supported, such as focal spots 402, 404, 406, and 407 of FIG. 4, and/or the focal spot sizes described in reference to FIGS. 6 and 7.

The focal spot size may be selected based on a current applied to the cathode during the current view, in accordance with the mA modulation profile. In various embodiments, the current applied during the current view may be compared to a plurality of current thresholds that define current ranges. For example, if the current applied is less than a first threshold current value (e.g., 360 mA), a first focal spot size (e.g., first focal spot 402) may be selected for the current view. If the current applied is greater than a second threshold current value (e.g., 515 mA), a second focal spot size (e.g., second focal spot 404) may be selected for the current view. If the current applied is greater than a third threshold current value (e.g., 765 mA), a third focal spot size (e.g., third focal spot 406) may be selected for the current view, and so on.

At 808, method 800 includes focusing the electron beam at the selected focal spot on the target, using electrostatic and/or electromagnetic controls, for a duration of the view. Focusing the electron beam at the selected focal spot may include applying one or more voltages to one or more corresponding extraction and focusing electrodes of the X-ray tube (e.g., the one or more focusing electrodes 316 of FIG. 3A). In various embodiments, a first set of the one or more corresponding focusing electrodes may perform a first focusing of the electron beam, and a second set of the one or more corresponding focusing electrodes may perform a second focusing of the electron beam.

At 810, method 800 includes determining whether a current prescribed by the mA modulation profile at a subsequent view is within a same current range as the preceding view (e.g., the current view of step 808). During portions of the exposure, various consecutive views may be scanned at a same or similar current. During other portions of the exposure, the current prescribed by the mA modulation profile may vary between views or portions of view, where the prescribed current at the subsequent view may fall within a different current range than the preceding view (e.g., as seen in the aggressive mA modulation profile described in relation to FIG. 5). In some embodiments, tubes that provide true view-to-view mA control may be advantageously used to manage a fast transition from a first spot to a second spot at the boundary between supported mA ranges between consecutive projection views, and possibly changing at every projection view. X-ray tubes with traditional cathodes may be otherwise limited in the rate of change of mA because of the thermionics of the filament or emitter where the electron beam originates.

If at 810 it is determined that the current prescribed by the mA modulation profile at the subsequent view is within the same current range as the preceding view, method 800 proceeds back to 808, where method 800 includes focusing the electron beam at the subsequent focal spot. In other words, the focal spot size used for the preceding view may not be changed. Alternatively, if at 810 it is determined that the current prescribed by the mA modulation profile at the subsequent view is not within the same current range as the preceding view, method 800 proceeds to 812.

At 812, method 800 includes determining whether the CT scan has completed (e.g., whether the object has been scanned at all view angles). For example, the CT scan may be completed when a full rotation of a gantry of the CT system has rotated 360 degrees around the object.

If at 812 it is determined that the CT scan has not completed, method 800 proceeds to 814. At 814, method 800 includes selecting a different focal spot size for the subsequent view, based on the current prescribed by the mA modulation profile for the subsequent view, and method 800 proceeds back to 808 to refocus the electron beam based on the selected focal spot size.

Alternatively, if at 812 it is determined that the CT scan has completed, method 800 proceeds to 816. At 816, method 800 includes generating an image from projection data acquired using the differently sized focal spots.

At 818, generating the image from projection data acquired using the differently sized focal spots may include adjusting a resolution of the reconstructed image or images, for example, to produce isotropic resolution. Generating the image from the projection data may include a backprojection process of the image reconstruction. A typical reconstruction from projection views acquired with different focal spots as a function of current or angular position may produce images with non-isotopic spatial resolution, since views with a smaller focal spot may have higher resolution and views with a larger focal spot may have lower resolution. In some embodiments, during the backprojection process, a resolution of one or more views of the projection data through the object may be adjusted as a function of focal spot size for the projection view. For example, the projection view may be pre-filtered (e.g., a filter may be applied to the projection view) as a function of a known or estimated focal spot size for the projection view. In one embodiment, all the projection views used to reconstruct an image may be filtered to match a spatial resolution of a projection view at a given spot size (e.g. the larger spot size throughout the acquisition), such that the overall spatial resolution performance of the reconstructed image would match the spatial resolution of a scan done with the fixed given spot size throughout the acquisition. This can result in an isotropic spatial resolution of the reconstructed image overall, which may be desired.

Overall, pre-filtering projection data acquired with different focal spot sizes for purposes of reconstructing images with isotropic resolution allows for a simplification of the system calibration process, while conserving the same overall imaging performance characteristics for the data acquisitions.

Note also that the concept of pre-filtering projection views for isotropic spatial resolution of a reconstructed image from said projection views may be applied to scans completed with varying focal spot sizes generated either in a controlled manner or in an uncontrolled manner, as long as the effective focal spot size of the projection views can be characterized or estimated.

Thus, methods and systems are proposed herein for generating focal spots of different sizes, and/or adjusting a size of a focal spot of a CT system for different views within a single exposure, and/or adjusting the resolution of the reconstructed image or images. When mA modulation is used, a large focal spot may be used during portions of the different views where a high amount of current is used to generate an electron beam, to ensure that power limits on a surface of a target of the CT system are not exceeded. However, rather than using the large focal spot for other portions of the different views where lower amounts of current are used to generate the electron beam, smaller focal spots may be selected, for example, based on the power limits for the lower amounts of current. By using the smaller focal spots where permitted by the mA modulation, a spatial resolution of reconstructed images may be increased.

The technical effect of dynamically adjusting a size of a focal spot of a CT system for different views of a single exposure, based on an amount of current applied at the different views, is that a spatial resolution of images reconstructed from the different views may be increased.

The disclosure also provides support for a computed tomography (CT) system, comprising: an X-ray tube including a cathode and a target, and an X-ray controller including one or more processors having executable instructions stored in a non-transitory memory of the CT system that, when executed, cause the one or more processors to: during a first view of a CT scan of an object, focus an electron beam generated by the cathode at a first focal spot on a target of the X-ray tube, the first focal spot of a first size, during a second view of the CT scan, focus the electron beam at a second focal spot on the target, the second focal spot of a second size, the second size different from the first size, and reconstruct an image of the object from projection data including the first view and the second view. In a first example of the system, the CT scan is an mA modulated scan. In a second example of the system, optionally including the first example, the first view and the second view are within a continuous X-ray exposure. In a third example of the system, optionally including one or both of the first and second examples, the first size is selected based on a first amount of current applied to the cathode in accordance with an mA modulation profile, and the second size is selected based on a second amount of current applied to the cathode in accordance with the mA modulation profile, the second amount different from the first amount. In a fourth example of the system, optionally including one or more or each of the first through third examples: the first size is selected to be a smallest size possible for the first amount of current that does not exceed a power limit for an amount of concentrated energy within the first focal spot on the target, and the second size is selected to be a smallest size possible for the second amount of current that does not exceed a power limit for an amount of concentrated energy within the second focal spot on the target. In a fifth example of the system, optionally including one or more or each of the first through fourth examples, projection view data of the CT scan is divided into a plurality of groups of views, and the electron beam is focused to generate a focal spot of a same size within a group of views of the plurality of groups of views, and different sizes between the plurality of groups of views. In a sixth example of the system, optionally including one or more or each of the first through fifth examples, the different sizes of focal spots are selected from a number of available focal spot sizes configured for the CT system. In a seventh example of the system, optionally including one or more or each of the first through sixth examples: in a first condition, where an amount of current applied to the cathode at a view is the same as an amount of current applied to the cathode at an immediately preceding view, a size of a focal spot selected for the view is the same as a size of a focal spot selected for the immediately preceding view, and in a second condition, where the amount of current applied to the cathode at the view is different from the amount of current applied to the cathode at the immediately preceding view, the size of the focal spot selected for the view is the different from the size of the focal spot selected for the immediately preceding view. In a eighth example of the system, optionally including one or more or each of the first through seventh examples, a focal spot size is selected based at least partly on one of a view angle of the projection view and a specific portion of an anatomy of a subject being scanned by the CT system. In a ninth example of the system, optionally including one or more or each of the first through eighth examples: focusing the electron beam at the first focal spot further comprises performing a first adjustment to at least one of electrostatic controls and/or electromagnetic controls of the X-Ray controller, where performing the first adjustment to the electrostatic controls includes adjusting a first voltage delivered at an electrode of the CT system, and performing the first adjustment to the electromagnetic controls includes adjusting one or more currents delivered to one or more magnets of the CT system, and focusing the electron beam at the second focal spot further comprises performing a second adjustment to at least one of the electrostatic controls and/or electromagnetic controls, the second adjustment different from the first adjustment. In a tenth example of the system, optionally including one or more or each of the first through ninth examples, the first adjustment is based on the first amount of current applied to the cathode in accordance with a mA modulation profile, and the second adjustment is based on the second amount of current applied to the cathode in accordance with the mA modulation profile. In a eleventh example of the system, optionally including one or more or each of the first through tenth examples, prior to initiating the CT scan, the CT system is calibrated for a plurality of different focal spots, each different focal spot corresponding to an exclusive current range at which the focal spot is used. In a twelfth example of the system, optionally including one or more or each of the first through eleventh examples, calibrating the CT system for the plurality of different focal spots further comprises calibrating the CT system for a corresponding current range of each focal spot of the plurality of different focal spots, and not calibrating the CT system for the focal spot for current ranges outside the corresponding current range.

The disclosure also provides support for a method for a computed tomography (CT) system, the method comprising: reconstructing an image of a scanned object from projection view data acquired during a scan performed by the CT system, wherein: the image is reconstructed from a first portion of the projection view data, the first portion acquired using a focal spot of a first size, and a second portion of the projection view data, the second portion acquired using a focal spot of a second size. In a first example of the method, the first portion of projection view data is corrected using a first calibration vector, the first calibration vector selected based on the focal spot of the first size, and the second portion of projection view data is corrected using a second calibration vector, the second calibration vector selected based on the focal spot of the second size. In a second example of the method, optionally including the first example, the method further comprises: during a backprojection process of image reconstruction, adjusting a resolution of a projection view through an object scanned by the CT system as a function of focal spot size for the projection view. In a third example of the method, optionally including one or both of the first and second examples, adjusting the resolution of the projection view as a function of focal spot size further comprises pre-filtering the projection view as a function of a known focal spot size for the projection view to match a spatial resolution across a plurality of views.

The disclosure also provides support for a method, comprising: during calibration of a computed tomography (CT) system to focus an electron beam of the CT system on a target of an X-ray tube: performing a first calibration of the CT system for a first focal spot of a first size, for a first range of kV/ma settings, and not performing the first calibration on a second range of kV/ma settings, performing a second calibration of the CT system for a second focal spot of a second size, for the second range of kV/ma settings, the second range of kV/ma settings different from the first range of kV/ma settings, and not performing the second calibration on the first range of kV/ma settings. In a first example of the method, the method is applied to the X-ray tube to generate focal spots sized in accordance with specifications of the CT system. In a second example of the method, optionally including the first example, the method is applied to the CT system to generate a plurality of calibration vectors to be applied to correct projection view data acquired by the CT system, the calibration vectors generated as a function of a size of a focal spot.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A computed tomography (CT) system, comprising:

an X-ray tube including a cathode and a target, and an X-ray controller including one or more processors having executable instructions stored in a non-transitory memory of the CT system that, when executed, cause the one or more processors to:

during a first view of a CT scan of an object, focus an electron beam generated by the cathode at a first focal spot on a target of the X-ray tube, the first focal spot of a first size;

during a second view of the CT scan, focus the electron beam at a second focal spot on the target, the second focal spot of a second size, the second size different from the first size; and reconstruct an image of the object from projection data including the first view and the second view;

wherein;

the CT scan is an mA modulated scan, and the first size is selected based on a first amount of current applied to the cathode in accordance with an mA modulation profile, the second size is selected based on a second amount of current applied to the cathode in accordance with the mA modulation profile, the second amount different from the first amount, and a total number of views of the CT scan is divided into a plurality of portions of consecutive views, each portion of the plurality of portions based on a corresponding range of current values of the mA modulation profile, and the electron beam is focused to generate a focal spot of a different size for a duration of each portion.

2. The CT system of claim 1, wherein, prior to reconstructing the image, a plurality of projection views used to reconstruct the image are filtered to match a spatial resolution of a projection view at a larger spot size used throughout an acquisition performed using the CT system.

3. The CT system of claim 1, wherein the first view and the second view are within a continuous X-ray exposure.

4. The CT system of claim 1, wherein:

the first size is selected to be a smallest size possible for the first amount of current that does not exceed a power limit for an amount of concentrated energy within the first focal spot on the target; and the second size is selected to be a smallest size possible for the second amount of current that does not exceed a power limit for an amount of concentrated energy within the second focal spot on the target.

5. The CT system of claim 1, wherein the different sizes of focal spots are small, medium, large, and extra-large.

6. The CT system of claim 1, wherein the current value ranges are overlapping.

7. The CT system of claim 6, wherein an amount of current falls within two overlapping current ranges, and a focal spot size for the amount of current is selected based on an attenuation path length through a scanned object.

8. The CT system of claim 1, wherein:

focusing the electron beam at the first focal spot further comprises performing a first adjustment to at least one of electrostatic controls and/or electromagnetic controls of the X-Ray controller, where performing the first adjustment to the electrostatic controls includes adjusting a first voltage delivered at an electrode of the CT system, and performing the first adjustment to the electromagnetic controls includes adjusting one or more currents delivered to one or more magnets of the CT system; and focusing the electron beam at the second focal spot further comprises performing a second adjustment to at least one of the electrostatic controls and/or electromagnetic controls, the second adjustment different from the first adjustment.

9. The CT system of claim 8, wherein the first adjustment is based on a first amount of current applied to the cathode in accordance with a mA modulation profile, and the second adjustment is based on a second amount of current applied to the cathode in accordance with the mA modulation profile.

10. The CT system of claim 1, wherein prior to initiating the CT scan, the CT system is calibrated for a plurality of different focal spots, each different focal spot corresponding to an exclusive current range at which the focal spot is used.

11. The CT system of claim 10, wherein calibrating the CT system for the plurality of different focal spots further comprises calibrating the CT system for a corresponding current range of each focal spot of the plurality of different focal spots, and not calibrating the CT system for the focal spot for current ranges outside the corresponding current range.

12. A method for a computed tomography (CT) system, the method comprising:

reconstructing an image of a scanned object from projection view data acquired during an mA modulated scan performed by the CT system, wherein:

the image is reconstructed from a first portion of the projection view data, the first portion acquired using a focal spot of a first size, the first size selected based on a first amount of current applied to the cathode in accordance with an mA modulation profile, and a second portion of the projection view data, the second portion acquired using a focal spot of a second size, the second size selected based on a second amount of current applied to the cathode in accordance with the mA modulation profile, the second amount different from the first amount; and a total number of views of the CT scan is divided into a plurality of portions of consecutive views, each portion of the plurality of portions based on a corresponding range of current values of the mA modulation profile, and the electron beam is focused to generate a focal spot of a different size for a duration of each portion.

13. The method of claim 12, wherein the first portion of projection view data is corrected using a first calibration vector, the first calibration vector selected based on the focal spot of the first size; and the second portion of projection view data is corrected using a second calibration vector, the second calibration vector selected based on the focal spot of the second size.

14. The method of claim 12, further comprising, during a backprojection process of image reconstruction, adjusting a resolution of a projection view through an object scanned by the CT system as a function of focal spot size for the projection view.

15. The method of claim 14, wherein adjusting the resolution of the projection view as a function of focal spot size further comprises pre-filtering the projection view as a function of a larger focal spot size for the projection view to match a spatial resolution across a plurality of views.

16. A method, comprising:

during a scan performed using a computed tomography (CT) system:

dividing a total number of views of the CT scan into a plurality of portions of consecutive views, each portion of the plurality of portions based on a corresponding range of current values of an mA modulation profile of the scan, and focusing an electron beam to generate a focal spot of a different size for a duration of each portion;

performing a first calibration of a first portion of the plurality of portions using a first set of calibration vectors selected for a first focal spot of a first size, the first set of calibration vectors covering a first range of kV/mA settings; and performing a second calibration of a second portion of the plurality of portions using a second set of calibration vectors selected for a second focal spot of a second size, the second set of calibration vectors covering the second range of kV/mA settings, the second range of kV/mA settings different from the first range of kV/mA settings.

17. The method of claim 16, wherein the method is applied to the X-ray tube to generate focal spots sized in accordance with specifications of the CT system.

18. The method of claim 16, wherein the method is applied to the CT system to generate a plurality of calibration vectors to be applied to correct projection view data acquired by the CT system, the calibration vectors generated as a function of a size of a focal spot.

19. The CT system of claim 5, wherein:

in a first condition, in accordance with the mA modulation profile, the current varies over a narrower overall range of current values, and wherein:

the electron beam is focused at the focal spot of the small size for a first number of consecutive views within a first current range of the narrower overall range of current values, and the electron beam is focused at the focal spot of the medium size for a second number of consecutive views within a second current range of the narrower overall range of current values; and in a second condition, in accordance with the mA modulation profile, the current varies over a wider overall range of current values, and wherein:

the electron beam is focused at the focal spot of the small size for a first number of consecutive views within a first current range of the wider overall range of current values, the electron beam is focused at the focal spot of the medium size for a second number of consecutive views within a second current range of the wider overall range of current values, the electron beam is focused at the focal spot of the large size for a third number of consecutive views within a third current range of the wider overall range of current values, and the electron beam is focused at a focal spot of the extra-large size for a fourth number of consecutive views within a fourth current range of the wider overall range of current values.

20. The CT system of claim 19, wherein, in the second condition, the size of the focal spot of the electron beam is increased as the current increases, and the size of the focal spot is decreased as the current decreases.

* * * * *